United States Patent [19]
Schwartz et al.

[11] Patent Number: 6,015,387
[45] Date of Patent: Jan. 18, 2000

[54] IMPLANTATION DEVICES FOR MONITORING AND REGULATING BLOOD FLOW

[75] Inventors: Robert S. Schwartz, Rochester; Robert A. VanTassel, Excelsior; David R. Holmes, Rochester, all of Minn.

[73] Assignee: MediVas, LLC, La Jolla, Calif.

[21] Appl. No.: 09/044,631

[22] Filed: Mar. 19, 1998

Related U.S. Application Data

[60] Provisional application No. 60/041,172, Mar. 20, 1997.

[51] Int. Cl.$^7$ .................................................... A61B 5/02
[52] U.S. Cl. ..................... 600/504; 600/12; 73/861.08; 73/861.14; 73/861.18
[58] Field of Search ................................... 600/504, 505, 600/9, 12, 13, 14, 507, 409; 73/861.08, 861.11, 861.12, 861.14, 861.18

[56] References Cited

U.S. PATENT DOCUMENTS 3,487,826  1/1970  Barefoot ................................. 600/505
4,600,855  7/1986  Strachan ................................. 310/338
4,727,754  3/1988  Ruckel ................................. 73/861.12
5,636,638  6/1997  Carlson et al. ........................ 600/504

*Primary Examiner*—Cary O'Connor
*Assistant Examiner*—Navin Natnithithadha
*Attorney, Agent, or Firm*—Gray Cary Ware & Freidenrich; June M. Learn

[57] ABSTRACT

The present invention provides a blood flow measurement device for implantation either within or around a blood vessel. The invention blood flow measurement device comprises a hollow tubular body, such as a stent, having a sensor with a resonant circuit for establishing an electrical current flowing within the blood vessel. Once implanted and activated by an external power source, the flow of current in the circuit generates an electromagnetic signal indicative of the rate of blood flow in the associated vessel. The signal can be picked up by an external monitor to display blood flow information. Since blood flow information is obtained non-invasively once the device is implanted, the device can be used to monitor blood flow in a patient undergoing strenuous exercise, after having been given an appropriate drug, and the like.

21 Claims, 1 Drawing Sheet

IMPLANTATION DEVICES FOR MONITORING AND REGULATING BLOOD FLOW

RELATED APPLICATIONS

This application relies for priority upon U.S. provisional application Ser. No. 60/041,172 filed Mar. 20, 1997, now abandoned.

FIELD OF THE INVENTION

The current invention relates generally to devices and systems for monitoring and/or regulating blood flow in a blood vessel, and more particularly to devices and systems for measuring blood flow in a blood vessel in a non-invasive manner once the device has been implanted into or about the blood vessel.

BACKGROUND OF THE INVENTION

In the treatment of heart diseases it is important to determine the overall effectiveness of the heart as a pump, and also the ability of the blood vessels to carry blood to other organs. It is well known that blood vessels may be become clogged or the walls lined with atheromatous plaque causing a restriction of the blood flow. If the blood flow within a vessel is significantly restricted, organs that depend on that flow may be damaged, and if the flow is stopped death may occur. Consequently, the measure of the blood flow within a blood vessel has been used as an indicator of the condition of the blood vessel and the pumping action of the heart. By monitoring the blood flow of a patient, the early detection of a heart condition is possible, and preventive measures may be taken to address any problems. If the blood vessel is seriously clogged, angioplasty or a by-pass operation may be performed that utilizes a graft to circumvent the damaged vessel.

In overseeing the condition of a patient's blood vessel, a number of blood flow measurements may be needed, over time, to effectively monitor the patient's condition. One known method of monitoring the flow in a blood vessel involves the percutaneous application of an instrument to measure the flow. Such methods are termed "invasive" in that the body must be pierced in order to measure the flow. Clearly, invasive techniques to measure blood flow have a disadvantage in that the measurement must be taken under controlled conditions. For example, it becomes very difficult if not practically impossible to monitor blood flow during periods of increased exercise.

Considering the above, it is apparent that a device that non-invasively measures the flow of blood in a blood vessel is desirous. Such a device would be implanted subcutaneously within the vessel as a stent, and activated by an external power source to measure the flow of blood in the vessel. It would be advantageous for the device to communicate with an external blood flow monitor to display the blood flow information. Since the measuring process is completely non-invasive, this technique permits monitoring of the blood flow under more extreme conditions for the patient, such as undergoing strenuous exercise or after given an appropriate drug.

It is thus an object of the invention to provide a stent that may be implanted in or around a blood vessel to measure in a non-invasive manner blood flow through the vessel.

It is a further object of the invention to provide a stent that may be implanted in or around a blood vessel to measure blood flow in a non-invasive manner that is powered transcutaneously.

It is a further object of the invention to provide a stent that may be implanted around a blood vessel to measure blood flow in a non-invasive manner that includes a digital microchip having a memory to store patient data.

SUMMARY OF THE INVENTION

The present invention provides devices, and methods for measuring the flow of blood in a blood vessel in a non-invasive manner. A device in the form of a stent, graft or cuff is provided that is implanted in or around a blood vessel and that is powered externally to activate the taking of blood flow measurements. The results of the blood flow measurements are then displayed on a monitoring device.

This invention attains the foregoing and other objects with novel stent devices which are summarized as follows.

In one aspect of the invention, a hollow cylindrical device is provided that is suitable for implantation in or around a blood vessel of a patient. The device includes an electric circuit in the cavity of the cylinder that is powered externally to radiate transcutaneously an indication of the blood flow within the device. The electric circuit may be configured as a LC or RLC circuit, exhibiting resonance at a chosen frequency.

In a still further aspect of the invention, a hollow cylindrical device is provided that is suitable for implantation in or around a blood vessel of a patient. The device includes a piezoelectric crystal for generating an ultrasonic wave that is directed toward the blood vessel. The same or a second piezoelectric crystal is employed to detect the reflected vibrational wave from the blood vessel and produce an RF signal that is indicative of blood flow within the blood vessel. The device is powered externally to radiate transcutaneously an indication of the blood flow within the device, and an external monitor is employed to calculate and display the blood flow results.

The devices of the present invention can also provide a therapeutic function by applying heat or vibration to the blood to inhibit restenosis. In one embodiment, a feed-back control loop regulates the therapeutic functions based on measurements of blood flow.

BRIEF DESCRIPTION OF THE DRAWINGS

The foregoing and other objects, features and advantages of the invention will be apparent from the following description and the accompanying drawings, in which like reference characters refer to the same parts throughout the different views.

DESCRIPTION OF AN ILLUSTRATIVE EMBODIMENT

Figure 1:
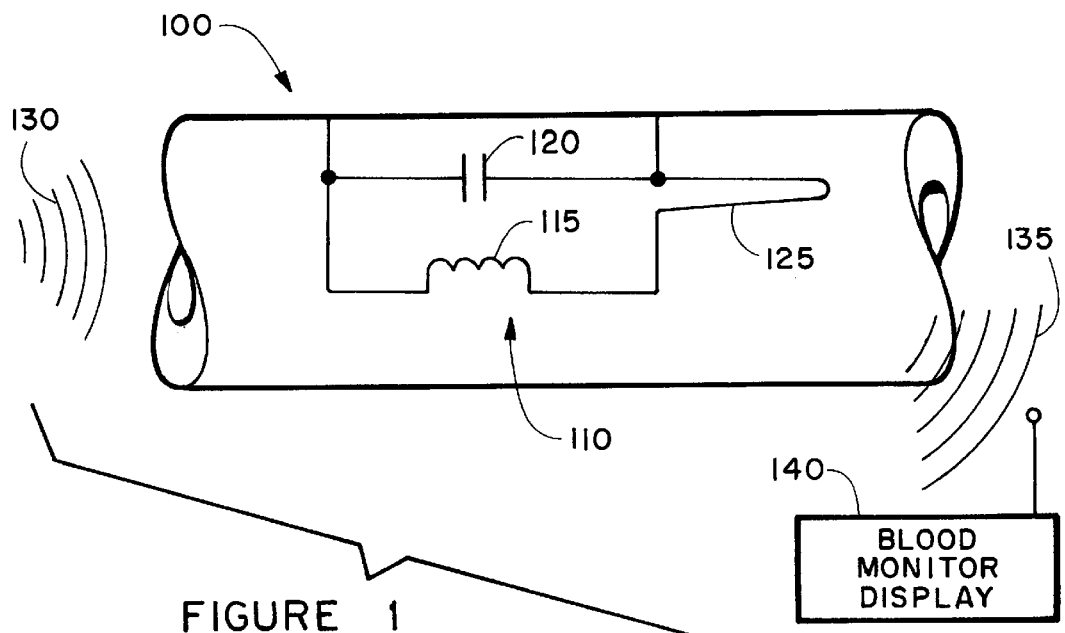
FIG. 1 is a cross-sectional view of a device having an LC circuit enclosed therein for measuring blood flow in a blood vessel, in accordance with the current invention.

Referring now to FIG. 1 which depicts a cross-sectional view of a stent in accordance with one embodiment of the invention, stent 100 is formed as a cylindrical, hollow tube of inert material suitable for implantation in a blood vessel of a patient. Stent 100 is open at both ends of the cylindrical tube to allow blood to flow through the stent. The outer diameter of the cylinder of stent 100 can be varied so as to fit within the blood vessel and to adapt to different blood vessel sizes. Similarly, the length of the stent can be varied according to need. The wall of the cylinder is sufficiently thin so as to not to significantly restrict the blood flow through the stent.

Stent 100 incorporates within the cylindrical cavity an electric circuit 110 that is activated to measure the blood flow of the patient. The blood flow measurements may be in the form of volume of flow/time or the velocity of the flow.

In one embodiment of the invention, electric circuit 110 is a LC circuit, having a coil 115 with inductance L and a capacitor 120 with capacitance C. The resistance R is a property of the wire, but may also be configured as a discrete component. Electric circuit 110 is fixedly attached to the cylindrical wall of stent 100, and positioned within the cylindrical tube of stent 100 so as to not appreciably impede blood flow through the device. Electric circuit 100 includes an antenna 125, serially connected to coil 115 and capacitance 120, for radiating an electromagnetic wave 135. Blood flowing through stent 100 acts as a dielectric for electric circuit 110. In response to an electromagnetic wave of energy 130 that is generated externally to the body and communicated through the skin to activate circuit 10, antenna 125 radiates a wave 135 that is indicative of the velocity or volume of flow/time of the blood flowing in stent 100. The electromagnetic wave of energy 130 may be a series of digital pulses or a sinusoidal wave that are transmitted transcutaneously to power electric circuit 110. The radiated wave 135 can be sensed by a monitoring device 140 which is exterior to the body, and the response converted to a blood flow measurement by monitoring device 140.

In one practice of the invention, an electromagnetic wave of energy 130 is generated at a frequency to cause electric circuit 110 to "ring" at its resonant frequency. For exemplary purposes, a wire having a diameter of 0.0025 inches is used to create 10 layers of coils with each coil having 16 turns. It is found that to generate a resonant frequency of 100 MHz, a capacitance of approximately 200 pF is required. The inductance L of coil 115 and the capacitance C of capacitor 120 can be adjusted to generate a specific resonant frequency for electric circuit 110 when no blood is flowing through stent 100. The resonant frequency may be adjusted to match the Larmor precession frequency or resonance of the blood components (i.e. hydrogen or iron nuclei). In response to the blood flow which acts as a dielectric, electric circuit 110 resonates at a different frequency. The change in the resonant frequency of the circuit is directly proportional to the velocity of the blood flow, and thus is an indicator of that velocity.

The progressive energy deposition at resonance is in turn shifted by the introduction of fresh blood flowing through the device. Alternatively, the energy deposition and permeability in the core of the stent are affected by the volume rate of flow in the device. Consequently, monitoring device 140 may use the calculated Q of the system to determine the volume rate of flow. Q, the quality factor for electric circuit 110, is proportional to the ratio of the maximum amount of energy stored in the circuit to the total energy lost per period. It is a measure of the energy deposition in the system. In another embodiment of the invention electric circuit 110 consists of a coil having inductance L and capacitance C. In this embodiment of the invention, electric circuit 110 does not include a lumped capacitance, but rather the capacitance is inherent in the wire implementing the coil.

Figure 2:
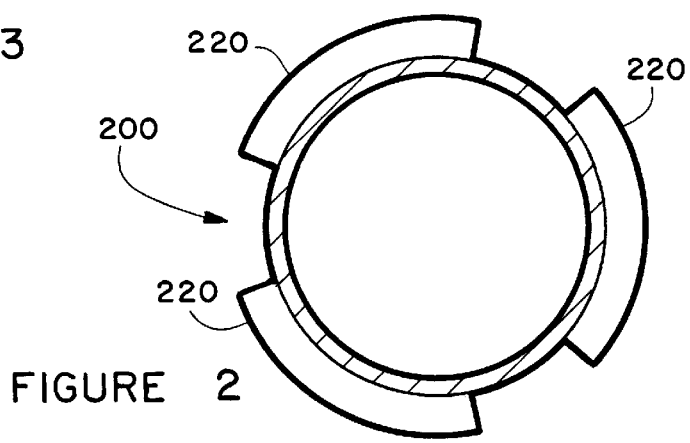
FIG. 2 is an end view of a device using having one or more microchips surrounding the stent for measuring blood flow in a blood vessel, in accordance with the current invention.

Referring now to FIG. 2, there is shown an alternate embodiment of the invention. A stent 200 for enclosing a blood vessel to monitor blood flow within a vessel is shown that includes one or more microchips 220 that are powered transcutaneously. The chip utilizes a coil to power the device and to transmit the radiated wave. Microchip 220 is advantageously fabricated using CMOS technology for low power consumption, and may be fabricated using VLSI. Microchip 220 includes a digital memory to store pertinent information about the device (i.e. serial number, blood flows recorded, patient's name, doctor's name, ect.). Again as described previously, stent 200 radiates a signal indicative of blood flow in the vessel. A monitoring device, exterior to the patient, detects the radiated signal and reports a measure of the blood flow.

Figure 3:
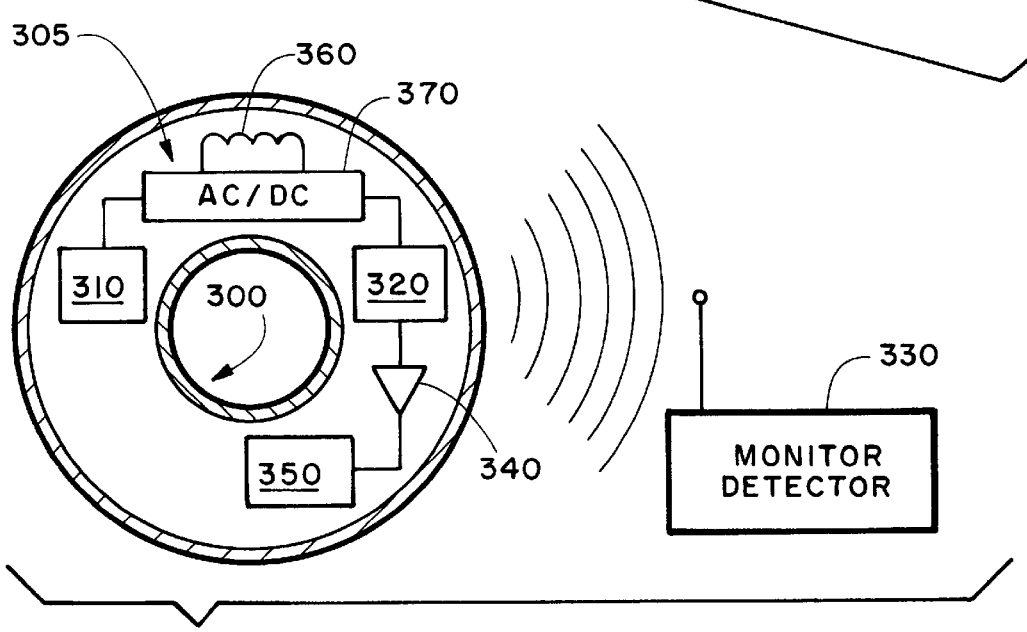
FIG. 3 is an end view of a device utilizing ultrasonic waves for measuring blood flow in a blood vessel, in accordance with the current invention.

In a further embodiment of the invention, FIG. 3 shows a stent 300 having a hollow, cylindrical shape suitable for implantation around a blood vessel. Stent 300 is open at both ends of the cylinder to allow blood to flow through the device. Component package 305 is attached to the outer wall of stent 300 for measuring blood flow and reporting the measurement transcutaneously. Piezoelectric crystal 310 is included in component package 305 for radiating, upon activation, the blood flow within the stent with an ultrasonic acoustic wave, and determining the rate of blood flow therefrom. The incident ultrasonic acoustic waves are partially reflected from the flowing blood, and the frequency of the reflected waves is altered according to the Doppler effect by an amount dependent on the blood flow velocity Thus the information as to the instantaneous flow velocity is contained in the reflected acoustic waves as a modulation of the waveform radiated by piezoelectric crystal 310. A second piezoelectric crystal 320 is included in component package 305 to receive the reflected ultrasonic waves from the radiation transmitted by piezoelectric crystal 310. Piezoelectric crystal 320 radiates a radio frequency (RF) signal analogous to the reflected ultrasonic wave. The RF signal is detected by a monitor detector 330, exterior to the body. Monitor detector 330 displays blood flow information corresponding to the RF signal. The RF signal generated by piezoelectric crystal 320 may be amplified by an amplifier 340 to boost the strength of the signal prior to transmission by another piezoelectric crystal 350. Stent 300 includes a coil 360 which is used to power the active components of the stent. An electromagnetic wave is transmitted transcutaneously to stent 300 to cause a current to flow in coil 360. The current from coil 360 drives an AC/DC converter 370 to power stent 300. Amplifier 330, coil 360, and AC/DC converter 370 may alternatively be packaged as an integrated circuit rather than implemented using discreet components. If the components are implemented using integrated circuit technology, it may advantageous to fabricate the circuit using a CMOS implementation for lower power consumption.

The devices of the present invention include thermal sensors and circuitry for the delivery of therapeutic heat or vibrations to the blood vessel in order to inhibit restenosis.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

We claim:

1. A blood flow measurement apparatus comprising:
   a hollow tubular body adapted for implantation within or around a blood vessel of a patient;
   a sensor circuit coupled to said tubular body, said sensor circuit including a resonant circuit and serving as a conduit for electrical current flowing in a circuit within the blood vessel;

whereby said flow of current generates an electromagnetic signal indicative of blood flow.

2. The blood flow apparatus of claim 1 further including a power coil coupled to said sensor circuit for receiving electromagnetic energy and powering said sensor circuit.

3. The blood flow apparatus of claim 1 wherein said tubular body is a stent.

4. The blood flow apparatus of claim 1 including a battery coupled to said sensor circuit for powering said sensor circuit.

5. The blood flow apparatus of claim 1 wherein said electromagnetic signal is a time varying magnetic field.

6. The blood flow apparatus of claim 1 wherein said electromagnetic signal is a time varying electric field.

7. The blood flow apparatus of claim 1 wherein said resonant circuit comprises an inductor and a capacitor coupled in parallel.

8. The blood flow apparatus of claim 1 further including an electromagnetic generator for generating said electromagnetic signal indicative of blood flow.

9. The blood flow apparatus of claim 1 wherein said electromagnetic signal indicative of blood flow is a radio frequency signal.

10. The blood flow apparatus of claim 8, wherein said generator is an antenna.

11. The blood flow apparatus of claim 1 where said tubular body encircles said coil.

12. The apparatus of claim 1 and further comprising means for applying therapeutic energy to the blood vessel.

13. A method of measuring blood flow within a blood vessel of a patient comprising the steps of:

a. inserting a hollow tubular stent containing a sensor circuit into said blood vessel;

b. energizing said sensor circuit and causing said circuit to generate an electromagnetic signal indicative of blood flow in said blood vessel;

c. non-invasively sensing said electromagnetic signal; and d. reporting said blood flow measurement corresponding to said electromagnetic signal.

14. The method of claim 13, wherein said sensor circuit contains a coil.

15. The method of claim 13, wherein said sensor circuit contains a coil and a capacitor in parallel.

16. The method of claim 13, wherein said electromagnetic signal is a time varying magnetic field.

17. The method of claim 13, wherein said electromagnetic signal is a time varying electric field.

18. A method of measuring blood flow within a blood vessel of a patient comprising the steps of:

a. inserting a hollow tube containing a sensor circuit into said blood vessel;

b. energizing said sensor circuit and causing said circuit to generate an acoustic signal indicative of blood flow in said blood vessel;

c. non-invasively sensing said acoustic signal;

d. reporting said blood flow measurement corresponding to said acoustic signal.

19. The method of claim 18, wherein said sensor circuit includes a piezoelectric crystal.

20. The method of claim 18, wherein radio frequency waves energize said sensor circuit.

21. The method of claim 20, wherein said sensing of said acoustic signal is by a piezoelectric crystal.

* * * * *